United States Patent
Van Ophuysen et al.

(10) Patent No.: US 12,109,083 B2
(45) Date of Patent: Oct. 8, 2024

(54) METHOD FOR MANUFACTURING A GLAZED DENTAL PROSTHESIS

(71) Applicant: INSTITUT STRAUMANN AG, Basel (CH)

(72) Inventors: Andreas Van Ophuysen, Basel (CH); Michael Graf, Basel (CH)

(73) Assignee: INSTITUT STRAUMANN AG, Basel (CH)

( * ) Notice: Subject to any disclaimer, the term of this patent is extended or adjusted under 35 U.S.C. 154(b) by 138 days.

(21) Appl. No.: 17/914,859

(22) PCT Filed: Mar. 29, 2021

(86) PCT No.: PCT/EP2021/058177
§ 371 (c)(1),
(2) Date: Sep. 27, 2022

(87) PCT Pub. No.: WO2021/198189
PCT Pub. Date: Oct. 7, 2021

(65) Prior Publication Data
US 2023/0065598 A1    Mar. 2, 2023

(30) Foreign Application Priority Data

Mar. 30, 2020   (EP) .................................. 20166730

(51) Int. Cl.
*A61C 13/09* (2006.01)
*A61C 13/00* (2006.01)
(Continued)

(52) U.S. Cl.
CPC .......... *A61C 13/09* (2013.01); *A61C 13/0006* (2013.01); *A61C 13/082* (2013.01); *A61C 13/083* (2013.01); *A61K 6/20* (2020.01)

(58) Field of Classification Search
CPC ... A61C 13/09; A61C 13/0006; A61C 13/082; A61C 13/083; A61C 13/0003; A61K 6/20
See application file for complete search history.

(56) References Cited

U.S. PATENT DOCUMENTS

| | | | |
|---|---|---|---|
| 990,320 A | | 4/1911 | Warren et al. |
| 5,089,306 A | * | 2/1992 | Grossman ............. B28B 11/044 428/35.1 |

(Continued)

FOREIGN PATENT DOCUMENTS

| | | | | |
|---|---|---|---|---|
| DE | 102010017407 A1 | * | 12/2011 | ........... A61C 13/082 |
| EP | 01 59 887 A2 | | 10/1985 | |
| WO | WO 2002 220 97 A1 | | 3/2002 | |

OTHER PUBLICATIONS

PCT International Search Report and Written Opinion for corresponding PCT Application No. PCT/EP2021/058177, mailed on Jun. 8, 2021, 10 pages.

(Continued)

*Primary Examiner* — Dah-Wei D. Yuan
*Assistant Examiner* — Nga Leung V Law
(74) *Attorney, Agent, or Firm* — Dority & Manning, P.A.

(57) ABSTRACT

In one aspect, a method for manufacturing a glazed dental prosthesis includes at least the steps of: a) providing a dental prosthesis body; b) position sensitive application of a predetermined amount of a glaze composition to at least a part of the dental prosthesis body surface, wherein the glaze comprises a heat sensitive coloring indicator and wherein this step is performed one or more times; c) controlling the applied glaze amount at least at one position of the glazed dental prosthesis body surface by assessing the color intensity at that position; and d) subjecting the coated dental body to a heat treatment to form the glazed dental prosthesis, wherein the temperature in the heat treatment is larger or equal to the de-composition temperature of the heat sensitive (Continued)

color indicator, wherein at least 90 mol-% of the coloring indicator are transformed into the colorless leuko-form.

15 Claims, 2 Drawing Sheets

(51) Int. Cl.
*A61C 13/08* (2006.01)
*A61C 13/083* (2006.01)
*A61K 6/20* (2020.01)

(56) References Cited

U.S. PATENT DOCUMENTS 6,740,267 B1    5/2004   Sekino et al.
2010/0297585 A1   11/2010   Yarovesky

OTHER PUBLICATIONS

Extended European Search Report for corresponding EP Application No. EP 20166730.0, dated Sep. 18, 2020, 7 pages.

* cited by examiner

METHOD FOR MANUFACTURING A GLAZED DENTAL PROSTHESIS

This application is a national phase application of International Patent Application No. PCT/EP2021/058177, filed Mar. 29, 2021, which, in turn, is based upon and claims the right of priority to European Patent Application No. 20166730.0, filed on Mar. 30, 2020, the disclosures of both of which are hereby incorporated by reference in their entirety for all purposes.

The present invention relates to a method for manufacturing a glazed dental prosthesis, wherein the method comprises at least the steps of: a) providing a dental prosthesis body; b) position sensitive application of a predetermined amount of a glaze composition to at least a part of the dental prosthesis body surface, wherein the glaze comprises a heat sensitive coloring indicator and wherein this step is performed one or more times; c) controlling the applied glaze amount at least at one position of the glazed dental prosthesis body surface by assessing the color intensity at that position; and d) subjecting the coated dental body to a heat treatment to form the glazed dental prosthesis, wherein the temperature in the heat treatment is larger or equal to the de-composition temperature of the heat sensitive color indicator, wherein at least 90 mol-% of the coloring indicator are transformed into the colorless leuko-form. The present invention further concerns a glazed prosthesis manufactured according to the inventive method.

The use of dental protheses in replacement of lost or broken teeth is not just a matter of aesthetics. Besides the task to maintain proper alignment and correct function of the jaws, it is furthermore of importance, that any secondary complications like tooth decay or infections based on ill-defined bite conditions or exposed root surfaces are avoided. Based on the fact that nowadays dental prostheses are able to provide long-term functional replacements, the desire in the market is additionally directed to technical solutions, also contributing to visually improved teeth appearance. In order to fulfil this task, one possible option in processing can be seen in controlling the outer prosthesis color and surface uniformity. An even and reproducible prosthesis surface improves the appearance, is able to prevent discolorations or plaque formation for a prolonged period of time and, in addition, is crucial for the mechanical protection of the inner prosthesis body.

Several attempts to improve or alter the optical properties of dental prosthesis can be found in the patent literature.

EP 01 59 887 A2, for instance, disclose a radiopaque dental composite, comprising a mixture of (a) polymerizable resin suitable for use in the oral environment, and (b) non-vitreous microparticles, wherein said microparticles individually comprise: (i) a plurality of amorphous microregions comprising oxide of silicon, substantially uniformly interspersed with (ii) a plurality of crystalline microregions comprising radiopacifying polycrystalline ceramic metal oxide, and said microparticles are substantially free of visually opacifying inclusions.

In addition, WO 2002 220 97 A1 disclose a method for bleaching teeth that have been discoloured by a staining agent, the method comprising the steps of coating an area of at least one tooth to be bleached with a dental bleaching composition and irradiating the coated area with laser energy for a predetermined period of time to activate an oxidising agent contained in the bleaching composition, the activated oxidising agent being capable of reacting with the staining agent to at least partly discolour the staining agent, characterised in that use is made of a laser emitting laser energy of a wave length capable of inducing a photochemical generation of radicals of the oxidising agent, which radicals in turn are capable of reacting with the staining agent to form a compound that is free of a conjugated electron system capable of absorbing visible light.

Furthermore, U.S. Pat. No. 990,320 disclose the manufacture of dental plates, wherein the process includes firstly coating the plate with opaque material, and subsequently adding a coating of translucent material tinted to match the gums.

Nevertheless, besides the already existing solutions in the field of dental prosthesis processing there still exists the need for further solutions, being able to provide functional and aesthetic dental prosthesis surfaces in a reproducible manner.

Therefore, it is the task of the current invention to overcome, at least in part, the drawbacks of the state of the art. Especially, it is a task of the invention at hand to provide a reproducible manufacturing process, directed to yield a homogeneous and evenly glazed dental prosthesis surface.

The above mentioned task is solved by a method comprising the features according to the independent claim 1. Preferred embodiments of the invention are also defined by the features of the dependent claims, by features disclosed in the description and in the figures, wherein a feature aggregation of separated parts is within the scope of the invention, unless explicitly excluded.

It is within the scope of the present invention to disclose a method for manufacturing a glazed dental prosthesis, wherein the method comprises at least the steps of:
  a) providing a dental prosthesis body;
  b) position sensitive application of a predetermined amount of a glaze composition to at least a part of the dental prosthesis body surface, wherein the glaze comprises a heat sensitive coloring indicator and wherein this step is performed one or more times;
  c) controlling the applied glaze amount at least at one position of the glazed dental prosthesis body surface by assessing the color intensity at that position; and
  d) subjecting the coated dental body to a heat treatment to form the glazed dental prosthesis, wherein the temperature in the heat treatment is larger or equal to the de-composition temperature of the heat sensitive color indicator, wherein at least 90 mol-% of the coloring indicator are transformed into the colorless leuko-form.

Surprisingly, it has been found, that via above described method it is possible to achieve homogeneous and uniformly glazed dental prostheses. The method is very flexible and several different prosthesis geometries can be manufactured. Within the process it can be assured, that spot specific on the surface the "right" glaze amount is applied. Therefore, the glazing step can be monitored and a prosthesis comprising an inaccurate glazing at any position of the prosthesis can be identified. These incorrectly glazed protheses can be subjected to an additional post-treatment or the out of specification material can be sorted out. In consequence, it is possible to reduce the overall amount of out of specification material by an automated process, thereby saving time and money. It is especially astonishing, that this is also possible for materials comprising difficult surface conditions like ceramics, wherein usually difficult and rough surfaces are achieved. At such difficult surface conditions, it could not be assumed, a priori, that an accurate quantitative assessment of a glaze is achievable.

The inventive method is a method for manufacturing glazed dental prostheses. By the inventive method it is for instance possible to manufacture glazed inlays, onlays, crowns, veneers, bridges, band on bridges, crowns on implants or bridges on implants. The dental prostheses are intended to be inserted in the mouth of a human or animal. The different dental prosthesis types all share the common feature, that they comprise one or more dental prothesis body parts. The parts may be based on the same or different materials and at least one of the parts comprises a glazing on at least a part of the surface.

In method step a) a dental prosthesis body is provided. The prosthesis body may be a finished prosthesis, ready for introduction into a patient's mouth, or it may be a pre-formed or near-final dental or orthodontic article subject to further processing before use. Therefore, the prosthesis body may be a partially or fully sintered dental prosthesis body. It is further possible, that the prosthesis body may comprise further surface coatings, wherein the additional surface coating is considered a part of the prosthesis body and the glazing is applied on top of the already present coating. The dental prosthesis can for instance be based on plastics, metal or an inorganic metal salt, a ceramic, porcelain or a glass ceramic in general. The aim of glazing is to seal the open pores in the surface of the dental prosthesis body and to produce a glossy surface.

In method step b) a predetermined amount of a glaze composition is applied position sensitive to at least a part of the dental prosthesis body surface. A glaze can be defined as a transparent or opaque glassy coating fired or otherwise fixed onto the surface of a dental prosthesis body. The glaze composition may comprise a mixture of ingredients from which the final coating or glaze is made. In addition, the glaze composition applied may comprise further components, for instance one or more solvents, wherein the further components will not form a part of the final coating and are removed in between application of the glaze composition and final glazing. Possible glazes may be "raw" or "fritted" glazes. "Raw" glazes may be composed of a mixture of finely ground insoluble natural materials—minerals and rocks such as china clay and nepheline syenite. Raw glazes are typically used at high firing temperatures (>1150° C.) on substrates such as porcelain (1300° C.). "Fritted" glazes are those where all or part of the ingredients have been prefused and quenched to form one or more frits. The frits are ground and mixed with other constituents (natural materials such as china clay) to formulate the final glaze composition. Fritted glazes can be used for ceramic ware and can be fired below 1150° C.

The glaze composition is applied position sensitive to at least a part of the dental prosthesis body surface. This means, that a predetermined amount of the glaze composition is applied to specific surface spots of the dental prosthesis body. The applied amount may vary with respect to the surface position or it is possible that the same glaze composition amount is applied to every surface spot to be glazed. The glaze composition amount may be defined in terms of an amount of glaze applied to a defined surface area. The amount may for instance be defined in g/cm². Based on the composition at hand this unit can further be mathematically transformed in a glaze thickness at this surface position. The glaze composition is applied position sensitive in cases, wherein the surface spot receiving the glaze composition is pre-determined. The surface spot may for instance be defined by the XYZ-coordinates of the dental prosthesis body surface.

The glaze composition applied in method step b) comprises a heat sensitive coloring indicator and this step is performed one or more times. Besides the glaze composition also a thermochromic paint or heat sensitive color substance is applied within the glaze composition. The thermochromic indicator is colored at the physical conditions, i.e. especially the temperature, at application onto the surface of the dental prosthesis body. This means, that the substance absorbs light of certain wavelengths and the absorption coefficient of the substance at this wavelength is known. The coloring indicator may be a pigment, a dye or a colored liquid crystal, wherein the indicator comprises the ability to alter the wavelength dependent absorption coefficient upon change of the physical surrounding. The position sensitive application in this step can be performed once or the application can be repeated two or more times.

In method step c) the applied glaze composition amount is controlled at least at one position of the glazed dental prosthesis body surface by assessing the color intensity at that position. The color intensity measurement can for instance be performed by measuring the reflected light intensity in response to an illumination of the surface spot with light of a predetermined wavelength. Therefore, preferably the reflected intensity is assessed. The color intensity may be assessed by a spectrophotometer or a camera system being calibrated to the absorption wavelength of the used color indicator. The color intensity on the surface can be measured at only one or at several spots on the surface. It is possible that a certain area is assessed at each spot, for instance in terms of mm², or it is possible to measure the response at several spots and perform an averaging of the different measurement outcomes. Besides assessing the color intensity of the surface spot, it is also possible to measure the response of the complete coating layer or the response of the coloring indicator in the coating layer. Therefore, it is also possible to assess the position sensitive coating thickness. The coating thickness can be assessed separately from the surface color intensity, only, or the thickness measurement can technically be based on the presence of the coloring indicator in the coating and can consequently be based on the same measurement principle. Generally, it is possible to assess the thickness by optical or other physical methods. For instance, it is possible to assess the thickness by methods based on the magnetic or inductive property differences of the prothesis surface and the glazing composition. Further methods might include X-ray reflectometry (XRR), X-Ray energy dispersion (ED-RFX) or coherent light interference spectroscopy. It is preferred, that the thickness assessment is based on optical methods, assessing the integral optical properties of the coloring indicator in the complete glazing composition layer and not only the response from the coloring indicator on the glazing surface. NIR-(near infra-red)measurements can be suitable for a variety of different coatings and dental prosthesis body materials.

In method step d) the coated dental body is subjected to a heat treatment to form the glazed dental prosthesis. In order to transform the glaze composition into a glaze, the glaze composition applied to the surface of the dental prosthesis body is heated or fired. Based on the heating the glaze composition alters its chemical appearance, e.g. by removal of solvents or by a chemical reaction between the glaze particles. Furthermore, based on the inorganic glazing components in the glaze composition a coherent glaze film is formed on the surface of the dental prosthesis body.

The temperature in the heat treatment is larger or equal to the de-composition temperature of the heat sensitive color indicator, thereby forming a leuko-form of the coloring indicator. Besides application of the necessary energy amount to transform the glaze composition in a glaze, the applied energy is at least also sufficient to change the chemical structure of the color indicator. As a consequence, the structure of the color indicator, and therefore also the light absorption behavior, is altered. The color indicator is transformed above the de-composition temperature into a colorless substance. The necessary energy for the chemical process can be expressed in terms of a temperature, wherein usually every color indicator comprises a de-composition temperature, indicating the loss of the ability to absorb electromagnetic waves at the wavelengths of the prior present absorption spectrum. The leuko-, i.e. the colorless, form of the coloring indicator is formed in cases, wherein at least 90 mol-%, preferably 95 mol-% and even more preferred 99,9 mol % of the coloring indicator are transformed into the colorless leuko-form. It is also possible, that temperatures are applied resulting in a complete de-composition, i.e. a burning, of the coloring indicator.

Within a preferred embodiment of the method the heat sensitive coloring indicator can be a dye. It has been found favorable that the color indicator is an organic dye and not an inorganic pigment. This is surprising, because the glaze composition is mainly based on inorganic particles. The coloring substance can be a dye as defined in ISO 18451-1:2019(E), wherein the dye is especially soluble in solvents. Suitable dyes can be organic molecules preferably comprising a molecular weight in the range of larger or equal of 50 g/mol and smaller or equal to 1000 g/mol.

In a preferred embodiment of the method the heat sensitive coloring indicator can be an alizarin derivative. Especially alizarin derivatives have been found favorable in the context of dental prosthesis bodies, wherein the surface of the dental prosthesis body is based on a ceramic. The alizarin derivative is a dye and especially soluble in solvents compatible with the glaze composition. It has also been found, that these dyes do only marginally interact with the surface of the dental prosthesis body, resulting in a higher reproducibility of the color measurements. The alizarin compounds comprise high absorptions coefficients and are readily de-composable in the right temperature range during glaze formation. Therefore, only small dye quantities are necessary and no visually detectable traces remain after leuko-form and glaze formation. The alizarin derivatives are based on an anthraquinone backbone according to the following structure

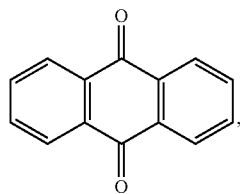 [SMILES: O=C1c2ccccc2C(=O)c2ccccc21]

wherein suitable alizarin derivatives at least comprise the following functional groups:

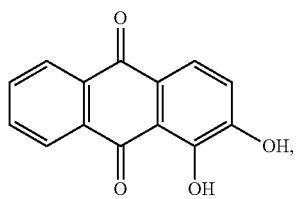 [SMILES: O=C1c2ccccc2C(=O)c2c1ccc(O)c2O]

wherein the hydroxy-moieties may be charged or un-charged, depending on the pH.

Furthermore, it is possible, that alizarin derivatives comprise one or two further functional groups at any suitable ring position, wherein $R^1$ and $R^2$ are independently an alkyl or a functional hetero-moiety comprising hetero-atoms like O, N, S or halogens:

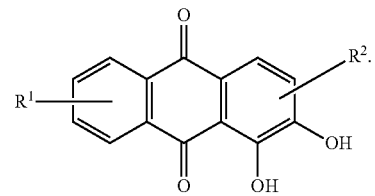

Examples of dyes comprising an anthraquinone backbone can for instance be dyes derived from cochineal. Possible dyes in the cochineal class can for instance be carminic acid or carmine including the salt forms, respectively. Further dyes can also be derived from cochineal, like cochineal red A also known as C.I. Acid Red 18 and denoted by the E-number E124 (1-(4-sulfo-1-napthylazo)-2-napthol-6,8-disulfonic acid, trisodium salt).

A suitable structure may for instance comprise a charged $SO_3$-moiety, like

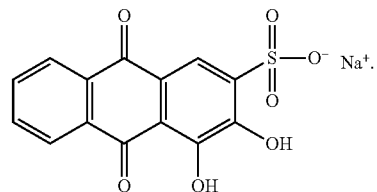

In addition, it is possible, that the alizarin derivative is incorporated in the glaze composition in a charged or protonated/de-protonated form, comprising different cations. Especially suited is alizarin, also known as 1,2-dihydroxyanthraquinone, Mordant Red 11, C.I. 58000 or Turkey Red.

Furthermore, in a preferred embodiment the coloring indicator can be an organic dye or pigment based on heterocyclic dilactam 2,5-dihydropyrrolo[3,4-c]pyrrole-1,4-dione (Diketopyrrolopyrrole or DPPs):

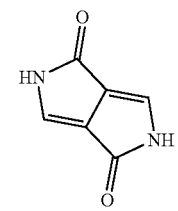

The DPP dyes are based on diketopyrrolopyrrole and the wavelength absorption behavior and the thermal stability can be adapted by changing the aromatic group at 3 and 6 positions. Electron donor groups, for instance thiophene, can be used to enlarge the conjugated system and results in an increase of emission wavelength. The derivatization with functional groups like C1-C4 alkyl, —OH, —CN, halogen, —NH₃ is also able to change the thermal stability of the dye in the background of a glazing composition. Thereby, the optical and thermal behavior can precisely be tailored with respect to the glazing composition and the dental prosthesis surface material. Preferably, the dilactam 2,5-dihydropyrrolo [3,4-c]pyrrole-1,4-dione structure can be used, because this dye may comprise a fairly low temperature stability in the range of 200° C. This low de-combustion temperature results in an easy thermal transformation of the coloring indicator into the leuko-from and results in a clear and transparent glazing.

Within a preferred aspect of the method the position sensitive application of the glaze in method step b) can be performed by spraying. To apply the glaze composition, it has been found suitable, that thin layers of the composition are sprayed onto the dental prosthesis body. The advantage of thin layers is, that a very precise glazing can be achieved. Preferably, 1 to 6 layers can be sprayed to the dental prosthesis body to achieve a homogeneous and reproducible glazing.

Within a preferred aspect of the method the dental prosthesis body surface is a sintered ceramic. The quantification process of the coloring substance on the dental prosthesis body has been found very reproducible in cases, wherein a ceramic surface is present. The results are surprisingly better compared to other surfaces like metals or polymeric surfaces. Without being bound by the theory it is assumed that the inorganic particle mixture present in the ceramic surface contributes to a favorable absorbance and reflectance behavior compared to other surfaces. This result has especially been found with an alizarin dye.

In a further preferred aspect of the method the glaze composition applied in step b) may comprise a mixture of inorganic particles comprising a $SiO_2$ and $B_2O_3$ content of larger or equal to 50 weight-% and smaller or equal to 90 weight-%. It has been found, that the result of the color assessment and thus the determination of the applied glaze composition amount can also be influenced by the applied glaze composition itself. Especially glaze compositions comprising Si- and B-oxides in the above defined weight-ranges deliver very reproducible measurements. The determination of the position sensitive applied glaze composition amount can be performed very sensitively and this finding is helpful to reduce the necessary color indicator amounts. This result has especially been found with an alizarin dye.

In another preferred characteristic of the method the glaze composition applied in step b) may comprise a mixture of inorganic particles at least comprising $SiO_2$, $B_2O_3$, $Al_2O_3$, $Na_2O$ particles. It has been found, that the result of the color assessment and thus the determination of the applied glaze composition amount can also be influenced by the applied glaze composition itself. Especially glaze compositions comprising the above defined inorganic particle mixture deliver very reproducible measurements. The determination of the position sensitive applied glaze composition amount can be performed very sensitively and this finding can be used to reduce the necessary color indicator amounts. This result has especially been found with an alizarin dye.

In another preferred embodiment of the method the glaze composition applied in step b) comprises a mixture of inorganic particles at least comprising $SiO_2$, $B_2O_3$, $Al_2O_3$, $Na_2O$, $CaO$, $K_2O$, $SnO_2$, $BaO$, $MgO$, $ZnO$, $ZrO_2$ and $P_2O_5$ particles $SiO_2$, $B_2O_3$, $Al_2O_3$, $Na_2O$, $CaO$, $K_2O$, $SnO_2$, $BaO$, $MgO$, $ZnO$, $ZrO_2$ and $P_2O_5$ particles. It has been found, that the result of the color assessment and thus the determination of the applied glaze composition amount can be influenced by the applied glaze composition itself. Especially glaze compositions comprising the above defined inorganic particle mixture deliver very reproducible measurements. The determination of the position sensitive applied glaze composition amount can be performed very sensitively and this finding can be used to reduce the necessary color indicator amounts. This result has especially been found with an alizarin dye.

Within a preferred embodiment of the method the glaze composition applied in step b) may comprise a solvent selected from the group consisting of glycol ethers or mixtures thereof. It is very unusual, that glaze compositions comprise solvents. Usually the dry glaze composition is applied to the dental prosthesis body surfaces. For the process at hand it has been found, that the incorporation of the coloring substance can easily be achieved by using a solvent based glaze composition. Especially, glycol ethers are suitable in the process, because they allow a homogeneous distribution of dyes in the glaze composition. In addition, these solvents do not hinder or disturb the glaze formation. Highly homogeneous glazes can be achieved. This result has especially been found in combination with an alizarin dye.

In another preferred aspect of the method the solvent can be selected from the group consisting of di(propylene glycol) methyl ether, 1-methoxy-2-propanol or mixtures thereof. For the process at hand it has been found favorable, that the incorporation of the coloring substance can easily be achieved by using a solvent based glaze composition. Especially, the above mentioned ethers are suitable in the process, because they allow a homogeneous distribution of the dyes in the glaze composition. In addition, they do not hinder a suitable glaze formation. Highly homogeneous glazes can be achieved. This result has especially been found with an alizarin dye.

In a further preferred characteristic of the method the concentration of the coloring indicator in the glaze composition can be larger or equal to 0.01 weight-% and smaller or equal to 1.5 weight-%. In order to find the "right" amount of coloring indicator the above given weight range has been found beneficial. The color assessment is based on a sufficiently large signal and the overall amount does not interfere with the glaze formation. Therefore, lower concentrations may not be suitable for determination of the applied glaze composition amount within the necessary precision. Higher concentrations may result in glazes comprising inferior mechanical properties or comprising a residual staining after firing.

In another preferred embodiment of the method the color assessment in step c) can be performed by a camera. Especially, a camera-based system has been found advantageous in order to determine the applied glaze amount. The camera can comprise a fiber optics, allowing the position or spot-based determination of the color intensity. In order to check the applied amount of glazing composition at the specific surface spot it is possible to perform a calibration and to check whether or not the measured quantity is within the error level of the calibration. Furthermore, it is possible to assess different wavelength ranges with the camera and to measure the optical behavior based on the signal reflected from the dental prosthesis body. Therefore, besides the surface coverage also the thickness of the glazing layer can be assessed spot specific.

In another preferred aspect of the method the weight ratio of the inorganic particles and the solvent in the glaze composition applied in step b) can be larger or equal to 0.5 and smaller or equal to 4. This ratio between inorganic particles and solvent is able to provide the necessary viscosity for an automated spraying process and fast drying times. This ratio also is able to distribute the color indicator homogeneously in the glaze composition, thereby resulting in very reproducible color assessments.

Within a further preferred characteristic of the method the heat treatment in step d) can at least partially be performed at a temperature of above or equal to 500° C. and below or equal to 1000° C. The above given temperature range has been found suitable for transforming the color indicator into the leuko-form and for achieving a glaze, comprising the intended mechanical stability. Lower temperatures may result in a still remaining visible staining or tinting of the glaze by the color indicator. Higher temperatures may result in a lower mechanical glaze stability.

In a further preferred embodiment of the method in step b) can be repeated in cases, wherein in method step c) the measurement reveals that the applied coloring indicator amount is lower or equal to 90% of the predetermined coloring indicator amount. In order to reduce the overall amount of out of spec material at least a further application of glaze composition can be performed in cases, wherein the measurement reveals, that the necessary glaze composition amount is not applied to the dental prosthesis body.

It is further within the scope of the invention to use the inventive method for manufacturing a glazed dental prosthesis. The inventive method can especially be used for manufacturing dental prostheses.

The individual dental prosthesis can be manufactured in a highly automated process and based on the staining and control steps within the process the process outcome with respect to quality is optimized. Prostheses comprising an insufficient glazing can be detected and re-worked before the glazing step is finished. With respect to the further advantages of the inventive use it is especially referred to the advantages of the inventive method.

It is further within the scope of the invention to disclose a glazed prosthesis manufactured according to the inventive method. Especially prostheses can be glazed within an automatized method, wherein the automatization results in a more homogeneous glazing compared to the manual processes according to the state of the art. The glazing is very homogeneous and differences between inventively processed prostheses and state of the art prostheses can for instance be based on the standard deviation of the glazing thickness. Further advantages of the inventively glazed prostheses can be deduced from the advantages of the inventive method.

The present invention will be further described with reference to the following figures without wishing to be limited by them.

Figure 1:
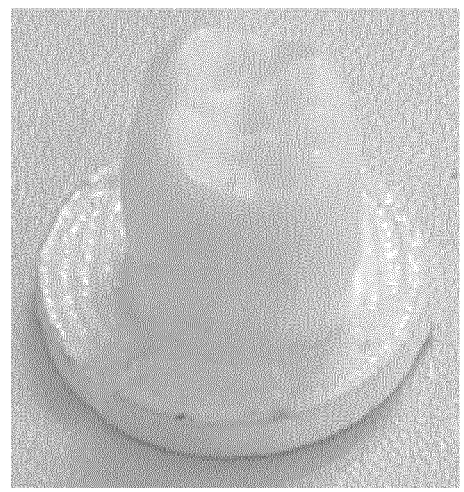
FIG. 1 shows a dental prosthesis body prior to a glazing step.

FIG. 1 shows a dental prosthesis body in the form of a sintered ceramic crown. The crown does not include a glazing and is attached to a baseplate. The crown composition is either based on a glass ceramic (e.g. lithium disilicate) or on a $ZrO_2$. In regard of $ZrO_2$ the ceramic is sintered at temperatures above 1000° C.

Figure 2:
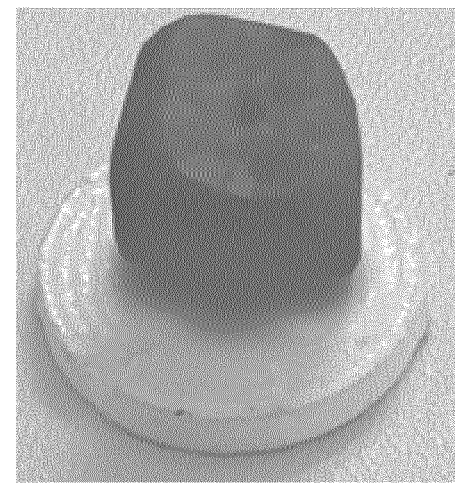
FIG. 2 shows a dental prosthesis body according to the invention after process step b) including the applied glaze composition including the coloring indicator.

FIG. 2 shows the crown depicted in FIG. 1 after process step b) according to the invention. The crown surface is covered with solvent based glaze composition comprising alizarin red as a heat sensitive coloring indicator after solvent removal. The surface is evenly coated with the glazing composition and therefore the surface appears in the black and white image darker. The glazing composition was automatically and position sensitively coated onto the prosthesis surface by a spraying robot. The spot sensitive coating can be performed in a single or multi-pass coating modus.

For instance, it is possible to perform one or up to 5 coating operations to coat a single surface spot. The measurement of the color intensity at different spots on the crown surface reveals, that the crown is evenly coated with the glazing composition. The color intensity at the surface was assessed using a camera system in reflectance.

Figure 3:
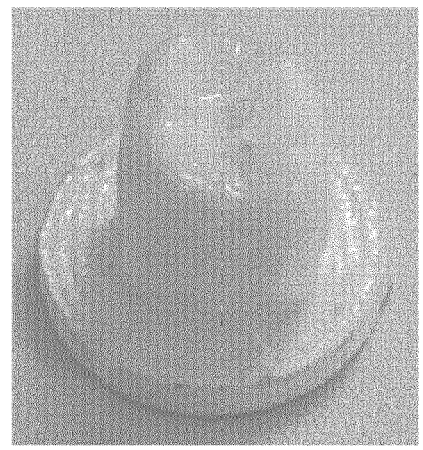
FIG. 3 shows a dental prosthesis body including a glazing according to the invention after process step d)

FIG. 3 shows the glazed crown of FIG. 2 after a thermal treatment at temperatures larger than 750° C. for more than 30 minutes. The thermal treatment can be adjusted as a function of time and temperature, wherein the combination of the parameter can be a function of the dental prosthesis material and the glazing composition. It can be seen, that after the thermal treatment the glazing is clear and colorless, indicating that the color indicator was transferred to the leuko-form. The mechanical properties of the glaze are unaltered compared to a standard glaze without the coloring indicator.

Figure 4:
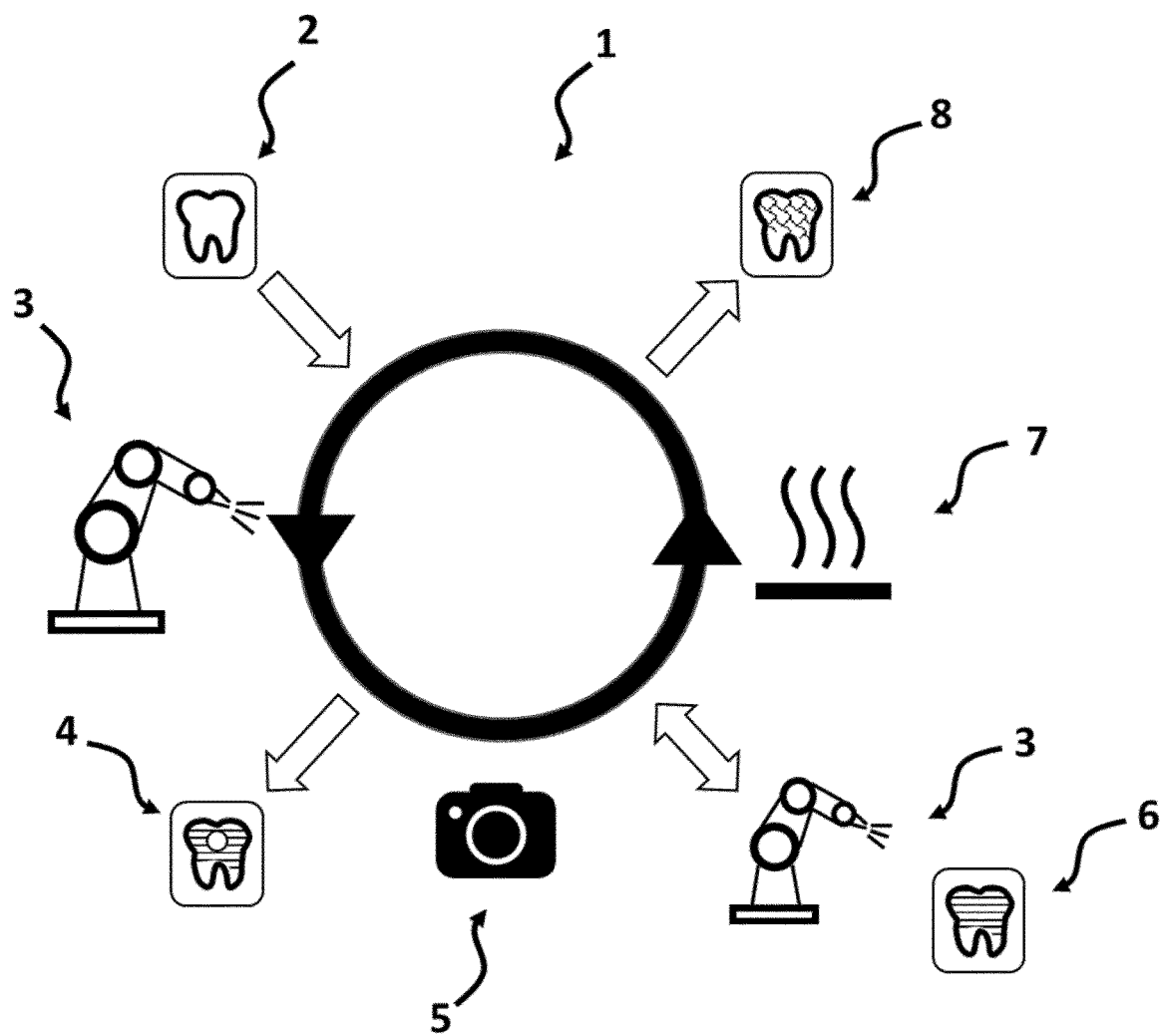
FIG. 4 shows an automated glazing process comprising the process steps according to the invention.

FIG. 4 shows an automated glazing process 1 comprising the process steps 3, 5, 7 according to the invention. At the beginning of the process 1, in process step a), a dental prosthesis 2 is provided. In this example the dental prosthesis 2 can be a sintered ceramic crown 2. The crown 2 can be provided on a base-plate as depicted in FIGS. 1-3. The crown 2 does not comprise a glazing at this stage. The crown 2 may be provided on a belt system, automatically transporting the crown to the different process stages. In process step b) the crown 2 can be presented to an automatic application or spraying system 3, wherein the spraying or application system 3 is configured to apply position sensitive a predetermined amount of a glazing composition onto the surface of the crown 2. The application can be performed in a single pass or the application can be repeated several times. The outcome of the application step b) is depicted by coated crown 4, partially comprising on the surface the glazing composition. The crown 4 comprises a surface spot, wherein no glazing composition was applied. The applied glazing composition comprises a color indicator, for instance a dye like alizarin red. Based on the dye the surface of the crown 2 is colored. The insufficiently coated surface spot does comprise less or no color at all. The coated crown 4 is transported to a camera system 5, wherein by the camera system 5 the color intensity on the crown surface 4 is assessed. The camera system 5 is able to assess whether or not the surface is colored at all or if enough glazing composition, i.e. the thickness of the glazing composition, is position sensitively applied. This assessment cannot be performed in cases, wherein no color indicator is present in the glazing composition, because the glazing composition is usually highly transparent and it is very difficult to assess visually, whether or not enough glazing composition is applied. The camera system 5 detects the insufficient coating based on the insufficient color intensity at this spot and the crown 4 is re-coated by a coating system 3, wherein the re-coating system 3 can be the same or a different coating system compared to the first coating system. The re-coated crown 6 now comprises a homogeneous coating on the crown surface. The success of the re-coating can further be monitored by the camera system 5. Based on the automatic control step it can be assured, that the re-coated crown 6 comprises spot sensitive the desired glaze composition amount. In process step c) the re-coated crown 6 is fired 7, transforming the glaze composition into a final glaze. During firing 7 the color indicator is transformed into a leuko-form, e.g. by complete combustion, resulting in a colorless glaze on the surface of the crown 8.

REFERENCE NUMERALS

1 Glazing Process according the Invention
2 Sintered Crown
3 Spraying Robot
4 Incompletely coated Crown
5 Camera System
6 Coated/re-coated Crown
7 Firing
8 Glazed Crown

The invention claimed is:

1. A method for manufacturing a glazed dental prosthesis, the method comprising at least the steps of:
    a) providing a dental prosthesis body;
    b) position sensitive application of a predetermined amount of a glaze composition to at least a part of the dental prosthesis body surface, wherein the glaze composition comprises a heat sensitive coloring indicator and wherein this step is performed one or more times;
    c) controlling the applied glaze composition amount at least at one position of the glazed dental prosthesis body surface by assessing the color intensity at that position; and
    d) subjecting the coated dental prothesis body to a heat treatment to form the glazed dental prosthesis, wherein the temperature in the heat treatment is larger or equal to the de-composition temperature of the heat sensitive coloring indicator, wherein at least 90 mol-% of the heat sensitive coloring indicator are transformed into a colorless form.

2. The method according to claim 1, wherein the heat sensitive coloring indicator is a dye.

3. The method according to claim 1, wherein the heat sensitive coloring indicator is an alizarin derivative.

4. The method according to claim 1, wherein the heat sensitive coloring indicator is a diketopyrrolopyrrole-derivative.

5. The method according to claim 1, wherein the dental prosthesis body surface is a sintered ceramic.

6. The method according to claim 1, wherein the glaze composition applied in step b) comprises a mixture of inorganic particles comprising a $SiO_2$ and $B_2O_3$ content of larger or equal to 50 weight-% and smaller or equal to 90 weight-%.

7. The method according to claim 1, wherein the glaze composition applied in step b) comprises a mixture of inorganic particles at least comprising $SiO_2$, $B_2O_3$, $Al_2O_3$, $Na_2O$ particles.

8. The method according to claim 1, wherein the glaze composition applied in step b) comprises a mixture of inorganic particles at least comprising $SiO_2$, $B_2O_3$, $Al_2O_3$, $Na_2O$, $CaO$, $K_2O$, $SnO_2$, $BaO$, $MgO$, $ZnO$, $ZrO_2$ and $P_2O_5$ particles.

9. The method according to claim 1, wherein the glaze composition applied in step b) comprises a solvent selected from the group consisting of glycol ethers or mixtures thereof.

10. The method according to claim 9, wherein the solvent is selected from the group consisting of di(propylene glycol) methyl ether, 1-methoxy-2-propanol or mixtures thereof.

11. The method according to claim 1, wherein the concentration of the heat sensitive coloring indicator in the glaze composition is larger or equal to 0.01 weight-% and smaller or equal to 1.5 weight-%.

12. The method according to claim 1, wherein color assessment in step c) is performed by a camera.

13. The method according to claim 6, wherein the weight ratio of the inorganic particles and the solvent in the glaze composition applied in step b) is larger or equal to 0.5 and smaller or equal to 4.

14. The method according to claim 1, wherein the heat treatment in step d) is at least partially performed at a temperature of above or equal to 500° C. and below or equal to 1000° C.

15. The method according to claim 1, wherein method step b) is repeated in cases, wherein in method step c) the assessment reveals that the applied heat sensitive coloring indicator amount is lower or equal to 90 mol % of the predetermined heat sensitive coloring indicator amount.

* * * * *